United States Patent [19]

Chauvin et al.

[11] Patent Number: 4,845,201

[45] Date of Patent: Jul. 4, 1989

[54] PROCESS FOR PRODUCING ORGANOLANTHANIDES, THE RESULTANT COMPOUNDS AND THEIR USE

[75] Inventors: Yves Chauvin, Le Pecq; Dominique Commereuc, Meudon; Francois Hugues, Nanterre; Helene Olivier, Rueil Malmaison; Lucien Saussine, Croissy Sur Seine, all of France

[73] Assignee: Institut Francais Du Petrole, Rueil-Malmaison, France

[21] Appl. No.: 146,752

[22] Filed: Jan. 22, 1988

[30] Foreign Application Priority Data

Jan. 22, 1987 [FR] France ............................... 87 00835
Dec. 9, 1987 [FR] France ............................... 87 17270

[51] Int. Cl.$^4$ .............................. C07F 5/00; B01J 31/12
[52] U.S. Cl. ..................................... 534/15; 585/469
[58] Field of Search ................ 534/15, 16; 502/151, 502/152, 155, 302, 303, 304

[56] References Cited

U.S. PATENT DOCUMENTS

Re. 29,368  8/1977  Pez ........................... 534/15 X
3,969,386   7/1976  Ballard et al. ............. 534/15
4,668,773   5/1987  Marks et al. ............... 534/15

OTHER PUBLICATIONS

Journal of the American Chemical Society, vol. 100, No. 1, (1978) pp. 331–333, "*Nonaqueous reductive lanthanide chemistry*".

Inorganic Chemistry, vol. 17, No. 3, (1978), pp. 625–631, DEKOCK et al. "Preparation, crystal and molecular structure . . . ".

Advances in Inorganic Chemistry and Radiochemistry vol. 14, (1972) Academic, Timms.

JACS 93:24 (Letters) p. 6687, Skell et al. Dec., 1971.

Advances in Organometallic Chemistry, vol. 5, 1977, Timms et al.

*Primary Examiner*—John F. Terapane
*Assistant Examiner*—Virginia B. Caress
*Attorney, Agent, or Firm*—Millen, White & Zelano

[57] ABSTRACT

A process for producing organolanthanides by reaction of a rare-earth metal with an unsaturated compound in an ether medium, the resultant compounds and the use of these compounds in organic synthesis and for catalysis is disclosed. The process is conducted at $-80°$ to $+100°$ C., in the absence of oxygen and any compound having active protons. The resultant compounds are useful as catalysts, e.g., in the hydrogenation of olefins and diolefins and in the polymerization thereof, and are useful as chemical intermediates.

11 Claims, No Drawings

PROCESS FOR PRODUCING ORGANOLANTHANIDES, THE RESULTANT COMPOUNDS AND THEIR USE

The present invention concerns a new process for producing organolanthanides having at least one metal-carbon bond, the new compounds obtained by this process and derivatives thereof, as well as the use of these compounds in synthesis and catalysis operations.

BACKGROUND OF THE INVENTION

The different ways presently known for obtaining divalent organolanthanides comprise:

either the reaction of an organometallic compound of the main series, such as an organosodium, an organolithium, an organomagnesium or an organoaluminum compound, with a lanthanide divalent salt such as a chloride, bromide or carboxylate;

or a transmetallation between the lanthanide metal, for example ytterbium, and an organomercuric compound, such as dicyclopentadienyl mercury;

or the dissolution of the lanthanide metal, such as europium or ytterbium for example, in liquid ammonia, followed by a reaction with a hydrocarbon containing an acid hydrogen (pKa<20) such as cyclopentadiene;

or the co-condensation, at low temperature, for example $-196°$ C., of metal vapor and of an unsaturated substrate.

The first two methods require the use of an organometallic compound obtained by other ways and then the separation of the by-products; the first two techniques are complex, the method with liquid ammonia giving amminated by-products and the vaporization method being limited by the metal amounts practically possible to vaporize. In addition, each of these methods leads only to the specific corresponding compounds.

SUMMARY OF THE INVENTION

It has now been found that an organolanthanide comprising at least one metal-carbon bond may be obtained by direct reaction of a rare-earth metal (or lanthanide) with a cyclic or acyclic organic compound comprising at least two unsaturations of the C=C, C=O and/or C=N type. The operation is conducted in an ether medium, in the absence of oxygen and of any compound with active protons, such for example as water, alcohol, ammonia. For example, with an unsaturated hydrocarbon, a compound having a hydrocarbon (molecule)/metal(atom) stoichiometry of 1/1 may be formed. By C=C saturation it is meant an ethylenic unsaturation and/or an aromatic unsaturation.

The unsaturated hydrocarbons to be used according to the invention are for example conjugated polyolefins, particularly conjugated di-, tri-, tetraolefins and aromatic hydrocarbons comprising several rings, preferably condensed.

The conjugated di-, tri-, tetraolefins are particularly those defined by the generic formulas:

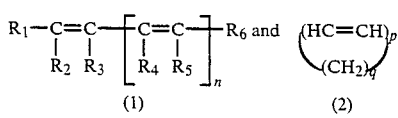

wherein n is an integer from 1 to 3, p an integer from 2 to 4, q being 0 or an integer from 1 to 5, the sum p+q being at least equal to 4.

In formula (1), $R_1$, $R_2$, $R_3$, $R_4$, $R_5$ and $R_6$, identical or different, are selected from the group consisting of the hydrogen atom and hydrocarbyl groups of 1–20 carbon atoms, for example alkyl, alkenyl, cycloalkyl, cycloalkenyl, aryl, aralkyl etc.. It is however preferable that $R_1$ or $R_2$ and $R_5$ or $R_6$ be hydrogen, so that the ending carbon atoms be not completely substituted.

The process is applicable to $C_4$–$C_{40}$ multiolefins. Examples of diolefins are butadiene, isoprene, piperylene, 2,3-dimethylbutadiene, 1-phenylbutadiene, 1,4-diphenylbutadiene, 1,3-cyclooctadiene. Examples of triolefins are 1,3, 5-hexatriene, 2,4,6-octatriene, 1,3,5-cycloheptatriene. An example of a tetraolefin is cyclooctatetraene.

Examples of condensed hydrocarbons to be used according to the invention and preferably containing 2-5 rings are napthalene, acenaphthene, acenaphthylene, anthracene, 9,10-dimethylanthracene, bis-9,10-trimethylsylilanthracene, phenanthrene, chrysene, pyrene and perylene.

Other compounds to be used according to the invention comprise ketones, particularly aromatic and conjugated olefinic ketones, and esters, particularly aromatic and conjugated olefinic esters.

The ketones preferably used according to the invention are monoketones of the general formula R COR$^1$(3), diketones of the formula RCO X COR$^1$ (4) and quinones of the general formula:

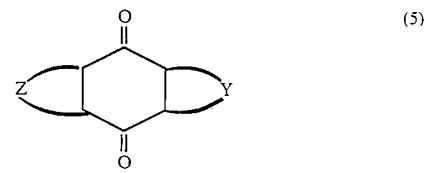

The preferred esters are those of general formula Ar-COOR (6)

In these formulas Ar is an aryl or alkylaryl radical containing 6–20 carbon atoms, R is either an Ar group as above defined or an alkenyl or cycloalkenyl group preferably containing 2–20 carbon atoms and $R_1$ designates a hydrocarbyl radical, particularly an alkyl, cycloalkyl, alkenyl, cycloalkenyl, aryl, alkylaryl or aralkyl radical containing 1–20 carbon atoms; X is a single bond or designates an alkylene group of 2–10 carbon atoms; Y and Z are a single bond or complete an aromatic ring, i.e. have the general formula CR=CR—CR=CR wherein R is a hydrogen atom or an alkyl radical.

Examples of benzophenone, chalcone, benzil, benzoquinone, naphthoquinone. The ester is for example phenyl benzoate or benzyl benzoate.

Compounds having one or several carbon-nitrogen double bonds in an acyclic or cyclic grouping, in particular the compounds in which said bond is conjugated with one or more carbon-carbon, carbon-oxygen and/or carbon-nitrogen double bonds and/or with one or more aromatic rings may also be added onto the rare-earths in ether medium. Examples of these compounds are quinoline, isoquinoline, acridine, phenazine, pyridazine, phenanthroline, azocines and Schiff bases resulting from the addition of an amine onto a ketone or an aldehyde such as benzilidene aniline.

The metals capable of reacting with the unsaturated hydrocarbons, unsaturated esters and nitrogenous unsaturated compounds are lanthanides, i.e. lanthanum and the metals which, in the periodic classification of elements, follow lanthanum, i.e. cerium, praseodymium, neodymium, samarium, europium, gadolinium, terbium, dysprosium, holmium, erbium, thulium, lutetium and ytterbium. Preferred are samarium, neodymium, cerium, europium and ytterbium. They are preferably used as a fine metal powder, cuttings or granules, and are previously activated by small amounts, for example of 0.1-10% in molar proportion to the metal, of hydrocarbyl halides, particularly alkyl, alkenyl, cycloalkyl, aryl or arylalkyl halides such as methyl iodide, methyl bromide, 1,2-diiodoethane or benzyl chloride, or halogen, preferably molecular iodine, mercury halides or rare-earth halides such for example as iodides.

The metal surface may also be activated by trituration or by the use of ultrasound.

The preferred medium wherein the metal is reacted with the unsaturated compound contains a mono or polyether having 2 to 20 carbon atoms. Preferred ethers are for example dimethylether, tetrahydrofuran, ethylene glycol dimethylether, diethylene glycol dimethylether, triethylene glycol dimethylether, ethylene glycol cyclic ethers comprising for example 4, 5, 6, 7 or 8 $-CH_2Ch_2O-$ recurrent units. Also cyclic or non cyclic ethers comprising one or several amine groups such as tris 2-(2-methoxy ethoxy)ethyl amine or cryptants may be used. These ethers may be used in admixture with one or more aliphatic, cycloaliphatic or aromatic hydrocarbons, for example heptane or toluene, in proportions by weight which depend on the ether, the ether/hydrocarbon ratio ranging for example from 0.1 to 10 or more, smaller ratios being preferably used with glycol cyclic ethers.

The volume of solvent, or of solvent mixture per gram of metal may range for example from 1 to 100 ml.

The molar ratio between the unsaturated organic compound and the metal may vary within wide limits, for example the ratio:gr.mol. of unsaturated compound/gr.at. of metal may vary from 1/20 to 20/1, preferably from 1/5 to 5/1. For favoring the conversion of the unsaturated organic compound, a metal excess will be used. Conversely, for favoring the metal conversion, an excess of unsaturated organic compound will be used.

The reaction temperature will preferably range from $-80°$ C. to $+100°$ C. It may be constant or may advantageously vary during the reaction. A higher temperature speeds up the reaction but may eventually disfavor the equilibrium and, above all, may lead to undesirable splitting reactions or dehydrogenation reactions of the ether used as solvent.

The reaction time, which depends on the temperature, on the surface state of the metal and on the nature of the medium, will be sufficient to convert the desired hydrocarbon proportion and may range for example from 1/2 hour to 48 hours. During the reaction the mixture will be advantageously stirred, mechanically or by ultrasound.

The pressure has no substantial effect on the reaction, provided that the unsaturated hydrocarbons and the ether form a liquid phase. The reaction may hence be performed under atmospheric pressure, but pressures from 1 kPa to 10 MPa may be used if necessary.

As the compounds formed are highly reactive with respect to oxygen and compounds with active protons, the preparation of the organolanthanide, the reaction and the separation of the products are performed in an inert atmosphere, for example under nitrogen or argon or under vacuum.

The obtained compounds may be freed from the solvent by settling or evaporation. They may be dissolved and recrystallized in a conveniently selected medium.

The rare-earth organometallic compounds object of the invention comply with formula $MR_x$ wherein R is defined as in the above formulas (1) to (6) and x is equal to 1, 2 or 3. They have the same applications as the previously known organolanthanides, but their selectivity is generally higher. Thus, by action of protonic derivatives such as water, alcohols and acids, they lead to hydrocarbons containing 2, eventually 4 hydrogen atoms in addition to those of the initial hydrocarbons, for example to dihydroanthracene by protolysis of the anthracenic complex. The deuteriolysis leads to di- or optionally tetra-deuteriated compounds. They react with ketones, aldehydes, esters, anhydrides, halogenated derivatives, sulfates and sulfides to give addition products which, by action of electrophilic agents lead to the corresponding reduced compounds. They may be used to catalyse the hydrogenation of olefins and diolefins and their polymerization.

By heating, the organolanthanides according to the invention lead to the formation of the corresponding metal in a very finely divided state, hence very reactive, for example with respect to hydrogen. From a mixture of compounds of several distinct metals, finely divided alloys may be obtained. Heating may be conducted in hydrocarbon medium, for example in boiling toluene.

EXAMPLES

The following examples illustrate the invention without limiting the scope thereof.

EXAMPLE 1

In a Schlenk tube, previously freed of oxygen and moistness, 20 m gr.atoms of ytterbium powder and 10 ml of ethylene glycol dimethyl ether (DME) containing 280 mg of 1,2-diiodoethane are introduced.

The reaction is continued under stirring at room temperature for one hour. The suspension is then cooled at $-20°$ C. and then 5 m.moles of anthracene, dissolved in 35 ml of DME, are added. After 20 hours of reaction at room temperature, a purple precipitate, characterized as being anthracene-ytterbium (1/1) solvated by DME, was formed with a substantially quantitative yield with respect to anthracene. The complex, treated with deuterizated methanol, gives 9,10-dideuteroanthracene with a quantitative yield ($>99\%$).

EXAMPLE 2

Example 1 is repeated, but with the use of 20 m.g atoms of samarium powder instead of ytterbium. Anthracene samarium (1/1) solvated with DME, is obtained as a purple compound with a substantially quantitative yield with respect to anthracene. The complex, treated with a water excess, gives dihydroanthracene with a quantitative yield.

EXAMPLE 3

Example 2 is repeated except that 5m.moles of 1,4-diphenylbutadiene are introduced instead of anthracene. A brown-red precipitate, characterized as being diphenylbutadiene-samarium (1/1) solvated with DME, is obtained with a yield of 43% with respect to the initial hydrocarbon. By suing an excess of methyl iodide, a mixture of isomers of dimethyl 1,4-diphenylbutenes have been obtained with a yield of 50%.

EXAMPLE 4

Example 1 is repeated except that anthracene is replaced by an equivalent molar amount of cyclooctatetraene. The resultant purple compound, obtained with a substantially quantitative yield, has been characterized as being cyclooctatetraeneytterbium solvated with DME.

EXAMPLE 5

Into a Schlenk tube, purged of oxygen and of moistness, are introduced 19 m.mole of ytterbium powder and then 10 ml of DME containing 1 m.mole of 1,2-diiodoethane. After reaction at room temperature for 1 hour under stirring, the mixture is cooled at $-78°$ C. and 5 m.moles of 1,3-butadiene gas is introduced. The tube is maintained for 20 hours within the range from $-78°$ C. to $-50°$ C. A grey precipitate, characterized as being butadiene-ytterbium (1/1) solvated by DME, is obtained with a 95% yield with respect to butadiene. The action of a methyl iodide excess has produced hexene isomers, in major art 3-hexene and 3-methyl 1-pentene.

EXAMPLE 6

Example 1 is repeated, except that anthracene is replaced with an equivalent molar amount of 1,4-diphenylbutadiene. A dark-red precipitate, characterized as being 1,4-diphenylbutadiene-ytterbium (1/1) solvated with DME, is obtained with a quantitative yield. The deuteriolysis of said compound leads to dideuterodiphenyl 1- and 2- butenes with a yield higher than 99%.

EXAMPLE 7

Into an autoclave of stainless steel of 100 ml volume capacity, previously freed from oxygen traces and from moistness, $5.8\ 10^{-4}$ mole of anthracene-samarium complex of example 2 is introduce, as suspension in 5 ml heptane. The pressure in the autoclave is brought to 4 MPa with ethylene at 25° C., then hydrogen is introduced so as to maintain the total pressure at 5 MPa. After stirring for 15 minutes, it has been observed that the gas no longer contained ethylene, the latter being converted to ethane; also high-quality polyethylene was formed.

EXAMPLE 8

Example 7 is repeated, but without hydrogen introduction. After 30 minutes of stirring, the autoclave contained 4 g of high-density polyethylene.

EXAMPLES 9 TO 20

The general operating mode used in these examples is as follows: A Schlenk tube, provided with a septum, purged of any trace of oxygen and moistness and maintained, all along the operation, under argon atmosphere, is charged with the selected metal amount. Then, 1,3 ml of dimethoxyethane (DME) containing 5 % by mole of 2,1-diiodoethane with respect to the metal, is introduced therein. After stirring of the medium for two hours at room temperature, the tube is cooled at $-20°$ C. and the selected amount of organic substrate, dissolved in DME, is added thereto. After one hour, the temperature is increased up to room temperature and the stirring is continued for 20 hours. The formed solution or suspension of organometallic compound is then treated with the appropriate reactant.

EXAMPLE 9

In accordance with above-described operating mode, 3 m.atoms of samarium powder are reacted with 1.4 mmole of benzophenone in 6.3 ml of DME. A first developed red color, which turned very dark-blue and then yellow-brown, characterized the obtained solution of samarium-benzophenone. After treatment with a methanol excess, solvent evaporation, dissolution of the metal in diluted sulfuric acid, extraction with diethylether, a product, characterized as being benzhydrol, is recovered quantitatively.

EXAMPLE 10

Example 9 is repeated; except that the samarium-benzophenone complex is treated with an excess of benzyl chloride. After treatments, the main isolated product is diphenylbenzylcarbinol, accompanied with 10% of triphenylethylene.

EXAMPLE 11

Example 9 is repeated except that 1.86 mmole of 2,6-diterbutyl anthracene is reacted with 7.45 m atoms of samarium powder, while stirring the medium by means of ultrasound. A purple viscous suspension of 2,6-diterbutyl-anthracene-samarium, so obtained in equimolecular proportions, was treated with 7.45 mmoles of acetone. From the medium 9,10-dihydro 2,6-diterbutyl (9-isopropylhydroxy) anthracene has been separated.

EXAMPLE 12

0.63 mmole of benzile is reacted with 2.73 m atoms of samarium powder in 7 ml of DME according to the same operating mode as in example 9. The color evolved from red to greenyellow, then to dark-green. The obtained solution contained benzile-samarium. By treatment with methanol, phenylacetophenone as well as smaller amounts of dihydrophenanthrene were formed.

EXAMPLE 13

0.77 mmole of chalcone are reacted with 3.07 m atoms of samarium powder in 6.2 ml of DME, according to the same operating mode as in example 9. The medium color has evolved from green to brown and then to red-orange, a solution of chalconesamarium being thus obtained. After action of methanol excess, a mixture of 1,3-diphenyl 1-propanone, 1,3-diphenyl 1-propanol and 1,3-diphenyl 2-propene 1-ol is recovered.

EXAMPLE 14

1.5 mmole of 1,8-dihexyl anthracene is reacted with 6.04 m atoms of samarium powder in 11 ml of DME, in the conditions of example 9. A dark-blue solution is obtained and freed, by filtration, from the metal excess. By solvent evaporation, a compound is obtained, whose elementary analysis corresponds to dihexylanthracene-samarium 1/1.

EXAMPLE 2.52 mmoles of benzile are reacted with 9.84 m atoms of neodymium powder in 15 ml of DME in the conditions of example 9. The color of the medium evolved from blue to red, then to green. A benzile-neodymium solution is thus obtained. After action of a methanol excess, followed with the usual treatment, phenylacetophenone (10%), benzoine (25%) and dihydrophenantrene (1%) have been isolated.

EXAMPLE 16

2.55 m atoms of ytterbium are reacted with 0.64 mmole of 2,6-dimethylanthracene in 8 ml of DME in the conditions of example 9 and 2,6-dimethylanthracene-ytterbium 1/1 is thus obtained. After action of an excess of deuteriated methanol and the usual treatment, 9,10-dideutero 9,10-dihydro 2,6-dimethyl anthracene has been quantitatively isolated.

EXAMPLE 17

1.16 mmole of cyclooctatetraene is reacted with 4.65 m atoms of cerium powder in 6.5 ml of DME with the same operating mode as in example 9. The obtained grey cerium cyclooctatetraene has been deuterolyzed with deuteriated methanol and then treated as above. Dideuterooctatriene, in the form of three isomers, has been thus obtained quantitatively.

EXAMPLE 18

1.14 mmole of anthracene is reacted with 4.57 m atoms of cerium as powder in 7.5 ml of DME in the conditions of example 9 with application of ultrasound, thus producing anthracenecerium. After action of a methanol excess and the usual treatment, 9,10-dihydroanthracene was isolated with a yield of 59%.

EXAMPLE 19

By reacting 1.38 mmole of 1,4-diphenyl 1,3-butadiene with 5.52 m atoms of cerium as powder in 8 ml of DME, with temporary application of ultrasound, a solution of 1,4-diphenyl 1,3-butadiene cerium has been obtained. AFter action of a methanol excess and the usual treatment, 1,4-diphenylbutenes (three isomers) were isolated with a yield of 295.

EXAMPLE 20

By reacting 0.85 mmole of phenyl benzoate in 6 ml of DME with 3.38 m atoms of samarium, in the conditions of example 9, a dark-brown compound (phenyl benzoate-samarium) has been obtained and treated as usually. Benzoate was quantitatively converted.

What is claimed is:

1. A process for producing lanthanide organometallic compounds, comprising reacting, in an ether medium, a metal of the lanthanide series with at least one unsaturated compound having at least two unsaturated bonds independently selected from the group consisting of $C=C$, $C=N$, and $C=O$, at a temperature from $-80°$ to $+100°$ C., in the absence of oxygen and any compound having active protons, wherein the metal of the lanthanide series is activated by a hydrocarbyl halide, a halogen, a mercury halide, a rare earth halide, trituration or ultrasound.

2. A process according to claim 1, wherein said unsaturated compound is selected from conjugated di-, tri- and tetraolefins of general formula:

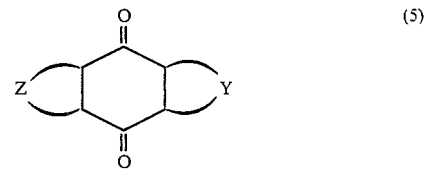

wherein $R_1$ to $R_6$ are selected from the hydrogen atom and hydrocarbyl radicals, n being an integer from 1 to 3, p an integer from 2 to 4 and q an integer from 1 to 5 or zero, the sum $p+q$ being at least equal to 3.

3. A process according to claim 1, wherein the unsaturated compound is an aromatic hydrocarbon comprising at least two condensed rings.

4. A process according to claim 1, wherein the unsaturated compound is a ketone of general formula $RCOR^1$, $RCOXCOR^1$ or a quinone of general formula:

(5)

wherein R is an aryl, alkylaryl, alkenyl or cycloalkenyl radical and $R_1$ is selected from hydrocarbyl radicals comprising 1–20 carbon atoms, X is a single bond or an alkylene group of 2–10 carbon atoms, Y and Z are a single bond or complete an aromatic ring.

5. A process according to claim 1, wherein the unsaturated compound is an ester of formula ArCOOR, wherein Ar is an aryl or alkylaryl radical of 6–20 carbon atoms and R a hydrocarbyl radical comprising 1–20 carbon atoms.

6. A process according to claim 1, wherein the unsaturated compound is quinoline, isoquinoline, acridine, phenazine, pyridazine, phenanthroline, azocine or a Schiff base.

7. A process according to claim 1, wherein the metal is samarium, europium or ytterbium.

8. A process according to claim 1, wherein the ether is selected from dimethylether, tetrahydrofuran, ethylene glycol, dimethylether, diethylene glycol, dimethylether and cyclic ethers of ethylene glycol comprising 4 to 8 —$CH_2 CH_2 O$— groups.

9. A process according to claim 1, wherein the ether medium comprises at least one hydrocarbon from the group of saturated hydrocarbons and aromatic hydrocarbons.

10. A process according to claim 1, wherein the reaction is conducted at $-78°$ to $-50°$ C.

11. A process according to claim 1, wherein the reaction is conducted at room temperature

* * * * *